US011150084B2

(12) United States Patent
Walter et al.

(10) Patent No.: US 11,150,084 B2
(45) Date of Patent: Oct. 19, 2021

(54) VERIFICATION METHOD

(71) Applicant: Nano-4-U AG, Samen (CH)

(72) Inventors: Harald Walter, Zurich (CH); Alexander Stuck, Wettingen (CH)

(73) Assignee: Nano-4-U AG, Samen (CH)

( * ) Notice: Subject to any disclaimer, the term of this patent is extended or adjusted under 35 U.S.C. 154(b) by 0 days.

(21) Appl. No.: 15/273,748

(22) Filed: Sep. 23, 2016

(65) Prior Publication Data

US 2017/0010091 A1 Jan. 12, 2017

Related U.S. Application Data

(62) Division of application No. 12/031,204, filed on Feb. 14, 2008, now abandoned.

(30) Foreign Application Priority Data

Feb. 16, 2007 (EP) .................................. 07003277

(51) Int. Cl.
| | |
|---|---|
| *A61J 3/00* | (2006.01) |
| *A61J 3/10* | (2006.01) |
| *A61K 9/20* | (2006.01) |
| *A61K 9/28* | (2006.01) |
| *G01B 9/02* | (2006.01) |
| *G01B 11/22* | (2006.01) |
| *A61J 1/03* | (2006.01) |

(52) U.S. Cl.
CPC .............. *G01B 11/22* (2013.01); *A61J 1/035* (2013.01); *A61J 3/005* (2013.01); *A61J 3/007* (2013.01); *A61J 3/10* (2013.01); *A61K 9/2009* (2013.01); *A61K 9/2013* (2013.01); *A61K 9/2018* (2013.01); *A61K 9/2054* (2013.01); *A61K 9/2072* (2013.01); *A61K 9/284* (2013.01); *G01B 9/02091* (2013.01)

(58) Field of Classification Search
CPC ...... G01B 11/22; G01B 9/02091; A61J 1/035; A61J 3/005; A61J 3/007; A61J 3/10; A61K 9/2009; A61K 9/2013; A61K 9/2054; A61K 9/2072; A61K 9/284
See application file for complete search history.

(56) References Cited

U.S. PATENT DOCUMENTS

| | | | |
|---|---|---|---|
| 4,484,797 A | 11/1984 | Knop et al. | |
| 4,904,675 A * | 2/1990 | Winter-Mihaly | C07D 213/80 514/227.5 |
| 5,135,812 A | 8/1992 | Phillips et al. | |
| 5,256,440 A | 10/1993 | Appel et al. | |
| 5,368,902 A | 11/1994 | Todd et al. | |
| 5,683,718 A | 11/1997 | Errigo | |
| 5,992,742 A | 11/1999 | Sullivan et al. | |
| 6,469,489 B1 | 10/2002 | Bourquin et al. | |
| 6,749,777 B2 | 6/2004 | Argoitia et al. | |
| 6,776,341 B1 | 8/2004 | Sullivan et al. | |
| 7,053,373 B1 | 5/2006 | Cleary | |
| 2002/0164456 A1 | 11/2002 | Souparis | |
| 2005/0279941 A1* | 12/2005 | Tsao | G01J 3/02 250/339.07 |
| 2006/0103130 A1 | 5/2006 | Koivukunnas et al. | |
| 2006/0246133 A1* | 11/2006 | Beasley | A61K 9/2054 424/468 |
| 2007/0285782 A1* | 12/2007 | Stuck | C09C 1/0015 359/569 |
| 2007/0286811 A1 | 12/2007 | Walter | |
| 2008/0057312 A1 | 3/2008 | Walter et al. | |
| 2010/0143467 A1 | 6/2010 | Stuck et al. | |

FOREIGN PATENT DOCUMENTS

| | | |
|---|---|---|
| FR | 2888491 A1 | 1/2007 |
| WO | 0110464 A1 | 2/2001 |
| WO | 03102084 A1 | 12/2003 |
| WO | 2004024836 A2 | 3/2004 |
| WO | 2005026848 A2 | 3/2005 |
| WO | 2006027688 A1 | 3/2006 |
| WO | 2006/047695 A2 | 5/2006 |
| WO | 2006047695 A3 | 11/2006 |
| WO | 2007144826 A2 | 12/2007 |

OTHER PUBLICATIONS

CAS No. 5989-81-1 Lactose Monohydrate, ChemNet.com, World Wide Chem Net, 1 page.
CAS No. 64044-51-1 (D-Glucose, 4-)-b-D-galactopyranosyl-, hydrat (1:1), Guidechem Chemical Trading Guide, 2 pages.
CAS No. 25249-54-1 (Polyvinulpyrrolidone cross-linked), Guidechem Chemical Trading Guide, 3 pages.
"Diffraction," Wikipedia, pp. 1-13 (2011).
EPO File History for European Patent No. 07 003 277.6.
Gale, M.T., "Zero-Order Grating Microstructures," Second Edition of Optical Document Security, pp. 267-287 (1998).
Gale, et. al., "Zero-Order Diffractive Microstructures for Security Application," SPIE vol. 1210, Optical Security and Anticounterfeiting Systems, pp. 83-89 (1990).
"Holography," Wikipedia, pp. 1-19 (2011).
Mashev, et. al., "Zero Order Anomaly of Dielectric Coated Grating," Optics Comm., 55(6), pp. 377-380 (1985).
Rosenblatt, et.al., "Resonant Grating Waveguide Structures," IEEE Jour. of Quan. Elec., 33(11), pp. 2038-2059 (1997).
U.S. Appl. No. 60/812,968 entitled "Realizing a diffractive microstructure in a pill survace" filed Jun. 13, 2006.
U.S. Appl. No. 60/812,967 entitled "Pharmaceutical pill with diffractive micro-structure" filed Jun. 13, 2006.
U.S. Appl. No. 60/812,957 entitled "Pill compressing tool comprising a diffractive micro-structure" filed Jun. 13, 2006.

(Continued)

*Primary Examiner* — Adam C Milligan
(74) *Attorney, Agent, or Firm* — Wood Herron & Evans LLP

(57) ABSTRACT

The present invention relates to a verification method of tablets, in particular pharmaceutical tablets. It further relates to an invisible secure marking or information which is a part of such tablet. The invention further relates to tablets suitable for such verification method, to processes for manufacturing such tablets and methods for reading the information.

9 Claims, 1 Drawing Sheet

(56) References Cited

OTHER PUBLICATIONS

Marques-Marinho, Flavia Dias, et al., "Cellulose and Its Derivatives Use in the Pharmaceutical Compounding Practice," IntechOpen (2013), available at https://www.intechopen.com/books/cellulose-medical-pharmaceutical-and-electronic-applications/cellulose-and-its-derivatives-use-in-the-pharmaceutical-compounding-practice (22 pages).

Schaafsma, G., "Lactose and lactose derivatives as bioactive ingredients in human nutrition," ScienceDirect, International Dairy Journal 18 (2008), pp. 458-465, Nov. 2007 (8 pages).

Thomas, Paul, "Split Decisions: Tablet Scoring Under More Scrutiny," Pharma Manufacturing, Jan 11, 2012, available at https://www.pharmamanufacturing.com/articles/2012/009/ (7 pages).

* cited by examiner

VERIFICATION METHOD

CROSS-REFERENCE TO RELATED APPLICATIONS

This application is a divisional application of U.S. patent application Ser. No. 12/031,204, filed on Feb. 14, 2008, which claimed priority to European Patent application no. 07003277.6, filed Feb. 16, 2007, the disclosures of which are incorporated herein by reference in their entireties.

BACKGROUND

The present invention relates to a verification method of tablets, in particular pharmaceutical tablets. It further relates to an invisible secure marking or information which is a part of such tablet. The invention further relates to tablets suitable for such verification method, to processes for manufacturing such tablets and methods for reading the information.

Forgery, grey market and illegal re-imports are considered an increasing issue in industry, in particular in the pharmaceutical industry, as many pharmaceutical products are targeted by forgers. This issue is getting more and more important for manufacturers, due to severe legal regulations which force the pharmaceutical companies to act against counterfeits. Many pharmaceuticals products are affected. This topic is not restricted to the third world, where the fraction of forged products in the supply chain is sometimes already above 50%. The problem reached the second and first world likewise, especially as pharmaceuticals are often much more expensive in more advanced economies. AIDS and cancer drugs are sometimes distinctly subsidized in developing countries, which enhances the danger of illegal re-imports.

Anti-counterfeiting features in the pharmaceutical market are typically applied to packages. For example holograms, optically variable inks, fluorescent dyes and other security features are attached to the packages, e.g. by adhesive tags. Alternatively such labels are laminated to the carton or are directly applied to the packages. The main drawback of such labels is that they can be removed from the product or the packaging. Further the tablets themselves are not marked, thus they can be easily separated from the package and repackaged.

Further, few approaches for secure labeling of tablets themselves are known, each suffering from various drawbacks.

Techniques based on forgery resistant signatures such as DNA of known sequence (U.S. Pat. No. 5,451,505) or molecules with characteristic isotopic composition or microparticles with characteristic color layer sequence (U.S. Pat. No. 6,455,157 B1) are considered unsuitable for pharmaceutical tablets, as these signatures are administered simultaneously by adding material to the original pharmaceutical recipe, which will require an additional regulatory approval.

Techniques based on a hologram on edible products are known. WO 01/10464 describes the coating of an edible product with a thermo formable and thus embossable layer. The tablets as disclosed in this document comprise a core, a coating and a microstructure at the surface of said coating. The diffractive microrelief is visible to the unaided eye and exposed to mechanical stress, like abrasion. The microreliefs as described in this document are considered very sensitive and may provide false results in verification methods. Still another drawback is that the described methods for implementing the diffractive relief structure in such tablets are not considered compatible with the existing mass production processes for solid pharmaceutical dosage forms (tablets).

WO2006/027688A1 describes an article, such as a tablet, having a visible diffractive microstructure on its surface or at an interface. Illuminated with white light the tablet shows a rainbow color effect similar to holograms. The diffractive microstructure can provide an indication of authenticity of the tablet. Although suitable for verification purposes, this document discloses a security element that is visible to the unaided eye. Second, a relatively large area of the tablet needs to be covered by the microstructure to obtain good results regarding visibility.

A number of optical detection devices useful for analyzing three-dimensional structures are known. Optical coherence tomography (OCT) is a known technique capable of visualizing three dimensional patterns, even if they are located at an interface below the surface of an article. The depth which can be visualized in a material depends on the optical properties of the material. It can be up to a few millimeters at present. U.S. Pat. No. 6,469,489 describes an array sensor which is used for parallel optical low-coherence tomography (pOCT) which enables real-time 3D imaging for topographic patterns. It provides three-dimensional and structural information with spatial resolution in the micrometer range. A plurality of electrical detection circuits with parallel outputs can form a one-dimensional or two-dimensional array sensor for the coherent or heterodyne analogue detection of intensity modulated optical signals simultaneously for all pixels with a high dynamic range. The array sensor may be used, e.g., in single or multiple wavelength interferometry, and especially in optical low-coherence tomography. It is known to use OCT for investigating the human skin, to control the quality of fast production processes like in die-bonding, in SMD pick and place systems, as well as mechanical inspection systems.

Altogether, there is a need for a secure marking of solid pharmaceutical dosage forms which does not change the composition of the tablets. There is also a need for a manufacturing process that is compatible with the existing processes for tablet mass production and which allows a secure marking of tablets. Further, there is a need for a verification method which is contact-less, fast and reliable.

SUMMARY

Thus, it is an object of the present invention to mitigate at least some of these drawbacks of the state of the art. In particular, it is an aim of the present invention to provide tablets, comprising an element of authenticity invisible to the human eye and a manufacturing process for such tablets. Further, it is an aim of the present invention to provide a verification method for tablets to determine the authenticity of such tablets avoiding the drawbacks of known verification methods.

These objectives are achieved by a tablet, in particular a pharmaceutical tablet, comprising one or more predetermined three-dimensional structures on its surface or below a coating wherein said predetermined structures are >2 μm in lateral direction and >50 nm in vertical direction and wherein said structures are invisible to the unaided eye and wherein said structures are detectable by an optical detection device, in particular by optical interferometry microscopy; a manufacturing process for producing the tablet comprising the step of embossing one or more of said predetermined structures on the surface of said tablet and optionally coating said tablet; and a verification method for a tablet, in particular a pharmaceutical tablet, wherein said tablet comprises one or more three-dimensional structures on its surface or below a coating wherein said structure is invisible to the unaided eye and wherein said method comprises the step of detecting said structure by means of an optical detection device. Further aspects of the invention are disclosed in the specification and independent claims, preferred embodiments are disclosed in the specification and the dependent claims.

The present invention will be described in more detail below. It is understood that the various embodiments, preferences and ranges may be combined at will. Further, depending on the specific embodiment, selected definitions, embodiments or ranges may not apply.

Unless otherwise stated, the following definitions shall apply in this specification:

The term "tablet" is known in the field. It relates in particular to a single solid dosage form comprising at least one solid active ingredient and optionally solid excipients (such as binders and other components). Tablets are usually manufactured by compacting, e.g. pressing, powders or granules of the respective components. The term "active ingredient" ("a.i."), as used herein, is not limited to a "pharmaceutical active ingredient" but includes all kinds of ingredients that are active, such as flavors, fragrances, active ingredients for animal health, active ingredients for plant protection. Further, tablets may be coated, resulting in a tablet comprising a core and coating. Pharmaceutical tablets are usually intended to be swallowed, and are therefore of a suitable size and shape.

An "element of authenticity" or "topography pattern" comprises one or more predetermined three-dimensional structures. Its presence proves authenticity of a tablet. Suitable structures are alphanumeric characters, logos, symbols and the like.

A "predetermined three-dimensional structure" denotes any structure detectable by an optical device. In one embodiment, such structure is non-periodic, i.e. it does not cause diffraction.

A "verification method" is a method that allows distinguishing genuine articles, such as tablets, from false articles.

BRIEF DESCRIPTION OF THE DRAWINGS

The figures attached to this specification are intended to further illustrate the invention, wherein.

DETAILED DESCRIPTION

Figure 1:
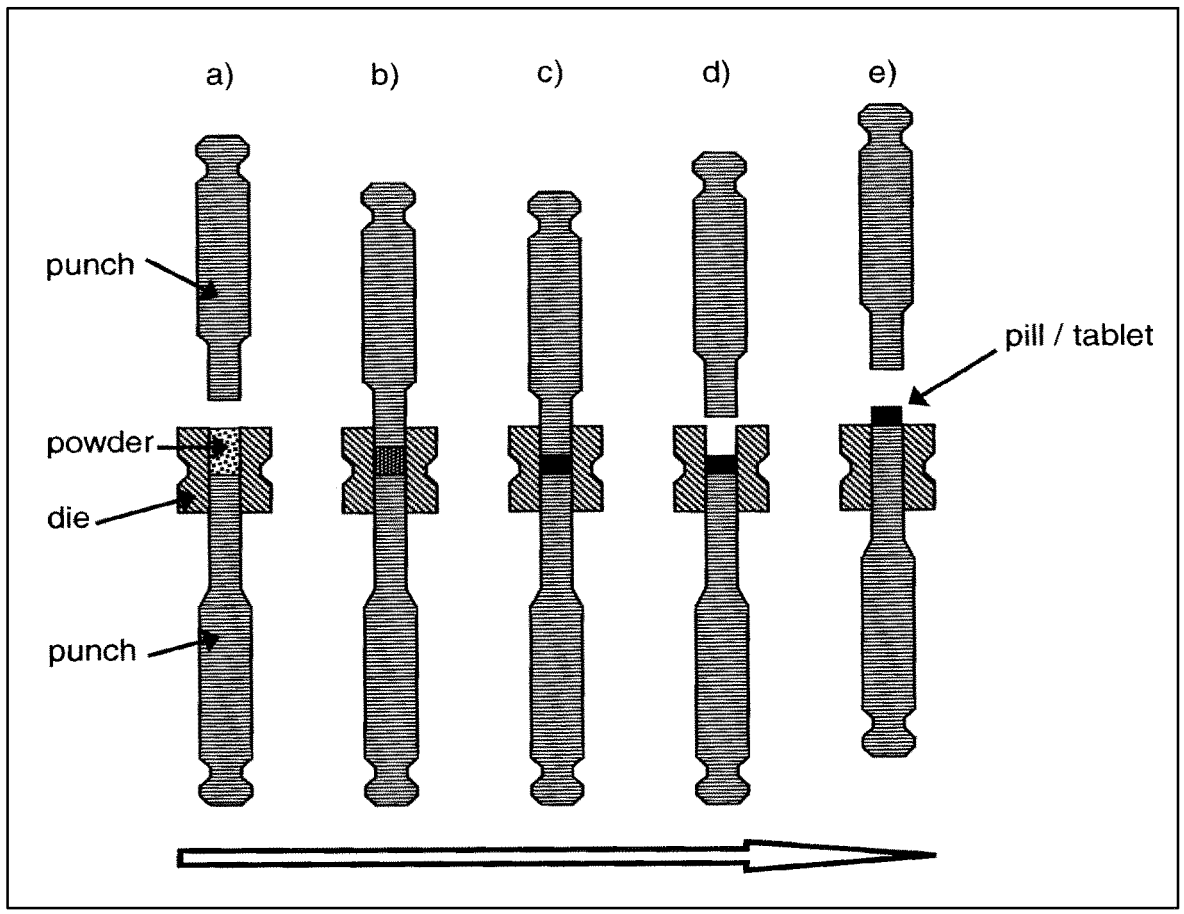
FIG. 1 is a schematic drawing of the tablet compacting process.

In a first aspect, the invention relates to a tablet comprising one or more predetermined three-dimensional structures on its surface or below a coating wherein said predetermined structure(s) is/are >2 µm in lateral direction and >50 nm in vertical direction and wherein said structure(s) is/are invisible to the unaided eye and wherein said structure(s) is/are detectable by an optical detection device.

In an advantageous embodiment, the optical detection device is an optical interferometry microscope.

The term tablet is known in the field and already defined above. Typically, a tablet is a mixture of at least one a.i. and excipients, usually in powder or granulated form, pressed into a solid. The mixtures consist of particles of different size, whereas the particle size distribution is considered critical for the compression process. A typical composition of such a powder mixture which is suitable for pharmaceutical tablets comprises 50-80% of a Lactose derivative (e.g. 73% Lactose Monohydrate), 10-50% of a cellulose derivative (e.g. 24% Microcrystalline Cellulose), 0.1-5% Silica, (e.g. 1% Aerosil (colloidal silica, anhydrous)), 0.1-5% of a fatty acid salt (e.g. 1% Magnesium-stearate) and 0.1-20% of a.i. (e.g. 1% a.i). Lactose and cellulose are the most widely used binding and filling agents, Aerosil improves the powder flow and Mg-stearate is used as a lubricant. The particle size distribution of the powder is usually 15-25% smaller than 75 µm, 30-50% in the range of 75 µm-150 µm, 15-25% between 150 µm-250 µm, 5-15% between 250 µm-500 µm and less than 2% larger than 500 µm.

In a further advantageous embodiment, the invention relates to a tablet as defined above wherein the powder or granules used in the manufacturing are coated with a binding agent. Improvements in the plasticity of a powder can be achieved by coating the particle surface with a plastic material. For example the particles can be partially coated with a binding agent like Polyvinylpyrrolidone (PVP), e.g., in wet granulation, which improves the compressibility of the particles. This, in turn, improves the quality of the three-dimensional structures embossed in the tablet.

In a further advantageous embodiment, the tablet comprises a pharmaceutically active ingredient ("pharmaceutical tablet" or "pill"). Pills are in particular subject to counterfeiting and authentication devices are therefore of particular relevance.

The predetermined three-dimensional structure may be any structure and is not limited to any periodicity or particular shape. Suitable are, for example, alphanumeric characters, geometric figures, bar codes, logos or combinations thereof. In one embodiment of the invention, said three-dimensional structure is non-periodic, i.e. it does not cause diffraction. The three-dimensional structure may either be an impression or a ridge or both, preferred are impressed three-dimensional structures.

In an advantageous embodiment, the predetermined three-dimensional structure is 2 µm to 50 µm (in particular 2 µm-20 µm) in lateral direction and 50 nm to 5 µm (in particular 50 nm-2 µm) in vertical direction. Structures of this size are detectable by an optical detection device and are typically invisible to the unaided eye. Such tablets are easy to manufacture, fully comply with existing manufacturing processes and can be distinguished from false products, e.g. by a method as described below.

In a further advantageous embodiment, the tablet comprises a core, a coating and one or more predetermined three-dimensional structures at an interface between core and coating wherein said structure is invisible to the unaided eye through the coating. The use of coatings is well known in the field and has many advantages such as improved handling, compliance, storage and better flavor. Further, a coating allows using larger three-dimensional structures, when compared with the uncoated tablet, as the coating covers such structures rendering them invisible. To ensure the three-dimensional structure is invisible through the coating the properties of said coating have to be adapted appropriately. Thus, the imprints/ridges formed by the embossing shall be smoothened by the coating. Further, invisibility of the structure is ensured by an appropriate color, thickness, reflection- or scattering-properties of the coating. Suitable parameters for a coating may be determined by the skilled person in routine experiments.

In a further advantageous embodiment, the tablet comprises a core, a coating and one or more predetermined three-dimensional structures at an interface between core and coating wherein said structure is invisible to the unaided eye through the coating and wherein the complex index of refraction (as defined in equation 1) of the coating and the complex index of refraction of the core differ.

$$\tilde{n} = n - iK \qquad (1)$$

In this equation, n is the real part, the so-called refractive index indicating the phase velocity v of the light (n=c/v), and K is the imaginary part, the extinction coefficient, which indicates the amount of absorption loss when the electromagnetic wave propagates through a material. The difference in the real part of this index is at least 0.04 and/or the difference in the imaginary part at least 0.02. Due to the difference in the complex index of refraction, such a tablet is in particular suitable for a verification method using an optical interferometry microscope. Suitable combinations coating/core may be determined by the skilled person in routine experiments.

In a further advantageous embodiment, the tablet as described herein additionally contains a visible interface, containing a pressed diffractive microstructure, e.g. a hologram. Such holograms are known and described e.g. in WO2006/027688 A1. In such a way, a tablet can be made, which has a visible as well as an invisible security feature on it. Thus, the invention relates also to a tablet comprising one or more predetermined three-dimensional structures as described herein and a diffractive microstructure.

In a second aspect, the invention relates to a verification method for a tablet wherein said tablet comprises one or more three-dimensional structures on its surface or below a coating, wherein said structure is invisible to the unaided eye and wherein said method comprises the step of detecting said structure by means of an optical detection device.

Said three-dimensional structure may be a predetermined structure, as described in connection with the first aspect of the present invention. Alternatively, said three-dimensional structure may be the structure obtained by a state-of the art manufacturing process for tablets. In this case, the characteristic surface of the embossing tools (the "fingerprint" of punch(es) and die) are transferred to the tablet causing a coarse structure. Said coarse structure is a three-dimensional structure within the context of this invention, but not a predetermined structure.

In a further advantageous embodiment, the invention relates to a verification method as described above further comprising the steps of recording a data set which describes characteristics of said structure by means of said detection device, and comparing the thus obtained data set with at least one predefined data set. Said predefined data set contains information on the predetermined three-dimensional structure and/or information on the fingerprint of the embossing tools used for manufacturing.

In a further advantageous embodiment, the invention relates to a verification method as described above, wherein said structure was obtained by an embossing method using an embossing tool, wherein said predefined data set comprises characteristics of an embossing surface of said embossing tool—the fingerprint—, and in particular wherein a plurality of predefined data sets is provided, each comprising characteristics of one of a plurality of embossing tools. This method allows authentication of tablets without any predetermined structure embossed in the tablet.

Suitable optical detection devices are known in the field. In principle, any optical detection device capable in detecting three-dimensional structures as defined above is suitable. Preferred devices are selected from the class consisting of optical interferometry microscopes. As the described secure marking or information is not visible for the human eye, a verification method is needed. Such method is preferably fast (i.e. it takes less than one second to distinguish forged from unique tablets). Optical interferometry microscopy offers all the features needed to measure the three-dimensional structures with the structure sizes mentioned above.

Figure 2:
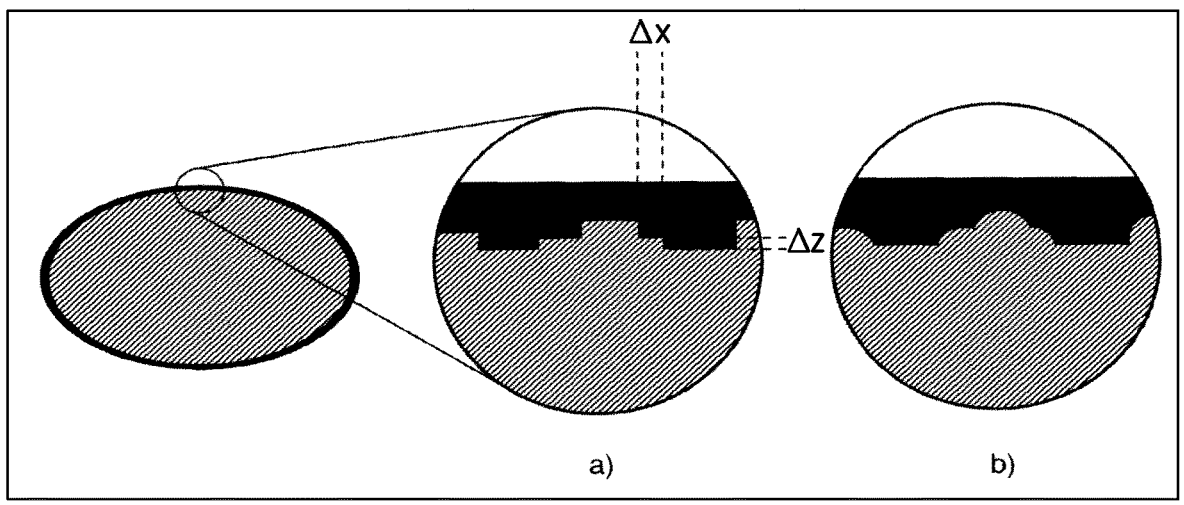
FIG. 2 is a schematic drawing of a coated tablet showing the predetermined three-dimensional structure invisible secure marking at the interface between tablet core and the tablet coating; wherein a) shows an angular shape of the structure, while b) shows a rounded shape of the structure.

In an advantageous embodiment of this invention optical detection devices are optical coherence tomographs. OCT is capable of visualizing three dimensional patterns with lateral resolution in the micrometer range even if they are located at an interface below the surface of an article. The depth which can be visualized in a material depends on the optical properties of the material. In absorbing or scattering light in the material it can be up to a few millimeters at present. OCT instruments with a low-coherence light source can distinguish objects in the vertical axis if their vertical separation amounts to at least a distance of the coherence length. Thus the minimal vertical distance of two interfaces corresponds to $L_c$ which is typically on the order of 1-10. The vertical resolution of structures at each interface is about 50 nm. The measured signal comes from a contrast in the complex index of refraction (see equation 1) at the interface. Both n and K are dependent on the frequency. The contrast can be in n or K or in both. As OCT is an interferometer based technology the contrast can be very low. Good signals are obtained even if the optical thickness (n×d) of a layer is about 2 μm. A major advantage of OCT is the possibility to detect three-dimensional structures through a typical tablet coating (=50 μm thickness) even if a colored coating is applied. A further advantage is the robustness with regards to the shape of the structure, in particular when compared to diffractive microstructures. The weak dissolving of the tablet core surface due to the water based coating solution is less critical; such dissolving will only lead to rounded edges (c.f. FIG. 2) whereas in the case of diffractive microstructures the diffraction efficiency drops down very fast. A basic OCT instrument is described in the U.S. Pat. No. 5,321,501. The low-coherence light reflected from the sample is combined with a reference signal, leading to an interferometry signal that is further processed to yield depth information.

In an advantageous embodiment of this invention optical detection devices are parallel optical coherence tomographs (pOCT), a specific OCT technique. A pOCT offers all the features needed to measure the topography pattern even at the interface between tablet core and tablet coating. It is known to use pOCT technique for investigating the skin of humans and to inspect the quality of fast production processes like in die-bonding, in SMD pick and place systems, as well as mechanical inspection systems. The OCT technique enables rapid 3D imaging of topographic patterns of diffuse and reflective media. It offers dimensional and structural information on a broad range of objects and materials with lateral resolution in the micrometer range. In more detail pOCT is even capable of measuring the internal structure of diffuse media. U.S. Pat. No. 6,469,489 describes a CMOS array sensor which is used for pOCT. Every single pixel of the array can acquire and process the optical signal in parallel. A plurality of electrical detection circuits with parallel outputs can form a one-dimensional or two-dimensional array sensor for the coherent or heterodyne analogue detection of intensity modulated optical signals simultaneously for all pixels with a high dynamic range. A single sweep of the reference mirror allows a scan of the complete sample and yields a full 3D tomography or topography image. This sensor provides 3-dimensional structural information with spatial resolution in the micrometer range. The array sensor may be used, e.g., in single or multiple wavelength interferometry, and especially in optical low-coherence tomography. pOCT offers the possibility to perform the verification in less than one second. Thus this technology can be used on-site. Even tablet verification at the pharmacies is thinkable.

In a further advantageous embodiment, the invention relates to a verification method as described above wherein the tablet is as defined in the first aspect of the invention.

In a further advantageous embodiment, the invention relates to a verification method as described above wherein said tablet comprises a core and a coating and wherein said predetermined structure is located at an interface between said core and said coating and wherein said method comprises the step of detecting said structure through said coating. To apply the verification method to a coated tablet is considered particular useful. Coated tablets are predominant on the market; the three-dimensional structure is protected against abrasion and direct inspection.

In a further advantageous embodiment, the invention relates to a verification method as described herein wherein said tablet is located in a blister. In this embodiment, verification of tablets takes place without unpacking the tablets. Blisters are typical packages for tablets, in particular pharmaceutical tablets. Thus, spot tests at distributors or pharmacies and the like are possible.

In a further advantageous embodiment, the invention relates to a verification method as described herein, wherein said tablet is located in a blister and said optical detection device is a OCT, especially a pOCT. OCT is a suitable detection method, as standard blister packages are transparent in the visible to NIR region (typically between 400 and 900 nm). Therefore even packaged tablets can be verified by OCT.

In a further advantageous embodiment, the invention relates to a verification method for a tablet (in particular a tablet es defined herein) comprising the step of analyzing (detecting and recording) said tablet by means of optical interferometry microscopy and comparing the thus obtained data set with a predefined data set.

As the size of the powder particles of the tablet is predominantly in the range of 75 μm-500 μm the topography structure is superposed with the grain structure of the particles. This has to be taken into account for the verification of the topography structure.

In a third aspect, the invention relates to processes for manufacturing tablets as described herein comprising the step of embossing one or more of said predetermined three-dimensional structures on the surface of said tablet and optionally coating said tablet. Said structure may be imprinted simultaneously with the embossing of the tablet or in a separate imprinting step. Preferably, embossing and imprinting take place simultaneously.

The process as described herein is fully compatible to the existing tablet manufacturing processes. Further, such process allows the use of a verification method which reads secure information contactless and very fast. The secure marking is based on a topography profile which is impressed in the surface of the tablet/the tablet core during the compressing process.

Tablets: The term tablet is known in the field and described above in more detail.

Tablet compression: The compressing of the powder mixture takes place in a die between two punches. (c.f. FIG. 1) The punches apply axial mechanical force. Typically the compression force is in the range of 5-25 kN. The powder fills the cavity which is sealed by the lower punch. The compressing time per tablet is very short in most production machines, typically <<100 ms. The production speed of state-of-the-art single rotary presses is up to 300,000 tablets per hour. The volume of the die defines the amount of powder which is compressed to form the tablet (FIG. 1a). This volume can be adjusted by the position of the lower punch during the filling of the cavity. Compression and consolidation, two interrelated phenomena take place simultaneously, (K. Marshall, "Tablet press fundaments", Tablets & Capsules 2005, p. 6-11). The former is a reduction in volume of the powder mass, the latter an increase in the mechanical strength of it. When the load is applied the volume of the powder decreases due to displacement of the air between the powder particles (FIG. 1b). This is called the repacking phase which is limited by the attainment of the closest possible particle packing arrangement and/or friction at the particle contact points. Next most materials begin to undergo elastic deformation until they reach their elastic limit (FIG. 1c). This phase is called yield stress phase. Beyond this phase, the components may undergo plastic and/or visco-elastic deformation. Without being bound to theory it is believed that the predetermined three dimensional structure (which provides the secure information) is mainly implemented in the pill or tablet surface by plastic deformation. In an advantageous embodiment a powder mixture or formulation can be chosen that provides a fraction of plastic deformable materials that is as high as possible while still fulfilling the requirements of the end product. For example, the fraction of microcrystalline cellulose or plastic binders such as PVP can be enhanced, or these materials can replace less plastic ones. At the end of the tablet press process the load is removed (FIG. 1d) and the finished tablet is ejected (FIG. 1e).

Tablet coating: Often a coating is applied after the compressing process resulting in a tablet comprising a core and a coating. Such coatings are applied for various reasons, e.g. to hide the taste of the tablet's components, to extend the shelf-life of components that are sensitive to moisture or oxidation or for compliance reasons. Coating materials are known in the field and include sugar-based coatings as well as polysaccharide and polymer coatings. Although sugar-coating was popular in the past, such coating has many drawbacks. Advantageous tablet coatings are polymer and polysaccharide based, with plasticizers and pigments included. The coating may be accomplished in conventional equipment, such as drum coaters. Tablet coatings must be stable and strong enough to survive the handling of the tablet, must not make tablets stick together during the coating process, and must follow the contours of macroscopic characters or logos on the tablets surface. Opaque or scattering materials like titanium dioxide can protect light-sensitive actives from photo degradation and also offer an opportunity to realize an attracting appearance of the tablet.

Thus, the invention relates in an advantageous embodiment to a process for manufacturing a tablet comprising the additional step of coating the tablet obtained by the above described process, with a conventional coating.

Invisible secure marking: The invisible secure marking is based on a predetermined three-dimensional structure which is embossed in the tablet/tablet core during the compressing process. For this the respective structure is transferred in the surface of the punch/punches or die used for tablet compressing. Such transfer is similar to the method for realizing a diffractive microstructure in the tablet core surface. In contrast to the diffractive microstructure the predetermined three-dimensional structure as defined herein does not need to be a periodical structure. It can be a 1d- or 2d-barcode, a logo, an alphanumeric character or nearly every pattern. Said structure may also be continuous on small scale (i.e. wavy), can contain wave like depth structures and the like. The restrictions to the pattern are minimum and maximum values for steps in x-/y- (lateral) and z-direction (vertical). While the minimum lateral step size $\Delta x$ and $\Delta y$ are the one for optical microscopes, thus >1 µm, the minimal vertical step size which can be resolved with OCT is on the order of 50 nm.

In an advantageous embodiment, the predetermined three-dimensional structure comprises plateaus with a vertical distance $\Delta z$ between each other of at least 50 nm (c.f. FIG. 2). Preferred are vertical distances $\Delta z$ between 100 nm and 15 µm, especially preferred between 200 nm and 7 µm. It was found that such plateaus are particularly suitable for detection by optical interferometry microscopy, especially by OCT. The height of the plateaus together with the two-dimensional pattern in x-/y direction can be measured to verify the three-dimensional invisible secure marking.

At the interface with the (predetermined) tree-dimensional structure a difference in the index of refraction and/or extinction coefficient and/or the scattering properties of the adjacent materials is required. For tablets bearing the topography pattern at the surface the contrast is the one between air and the powder material. As most tablets are coated the invisible marking must be measured through the approximately 50 µm thick coating. This can be achieved with the methods described herein, even if a colored coating is applied. In the case of coated tablets the contrast which gives the measured signal is the difference in the above mentioned parameters of the powder material and the coating material. The big advantage of this secure marking is that the measured signal does not rely on a very precise shape of the topography structure. In contrast even a minor erosion of diffractive microstructures reduces the optical effect monumental. Thus the weak dissolving of the tablet core surface due to the water based coating solution is less critical for the three-dimensional structures described in this document. The dissolving will only lead to rounded edges whereas in the case of diffractive microstructures the diffraction efficiency drops down very fast.

Manufacturing of embossing tools: As described herein, the manufacturing is fully compatible with state-of the art manufacturing processes for tablets. Either standard embossing tools or embossing tools comprising a predetermined three-dimensional structure are used for manufacturing tablets.

The predetermined three-dimensional structure can be implemented either in the punch surface of one or both punches and/or in the wall of the die used for manufacturing the tablet. As already mentioned the predetermined three-dimensional structure can be in the form of barcodes, logos, numbers, writings and the like. Such patterns can be implemented in the tool surface by known methods, e.g. dry- and wet- or spray-etching, laser ablation, mechanically engraving and the like. Dry etching in steel is described for example in the US2004/0032667A1, spray-etching in steel by S. Chatterjee et al in J. Micromech. Microeng. 16 (2006) p. 2585-2592 and micro-structuring of metal surfaces by laser ablation in Physik Journal 5 (2006) p. 16. Of course the scope of this invention is not limited to these methods. All methods capable of manufacturing topography structures with the lateral and vertical dimensions mentioned above are possible. Dry etching in steel can be done by depositing, e.g. spray- or spin-coating, a layer of resist on the tool surface, pattern the resist by illumination through a mask and developing the illuminated layer. The patterned layer acts as a mask in the dry etching step. If the lateral size of the desired topography pattern is compatible to the resolution of techniques like for example ink-jet-printing or tampon printing the patterned layer can be directly printed. To enhance the contrast in the dry etching step the resist layer can be coated before the developing step with a thin layer of a material which is etched very slowly. Examples of such materials are Chromium and Nickel. Evaporation or sputtering is widely used for the deposition of such materials. In this way deeper topography structures can be realized.

In an alternative embodiment the natural topography pattern of the tool surface (as it is after the tool manufacturing process) is used as a three-dimensional structure. In this case, the fingerprint of the embossing tools is detected in the verification method. For this each tool surface must be measured before or after the tools are used. This embodiment provides a signature of each tool (a "fingerprint") and thus a precise batch control. For applying a verification method to a tablet manufactured with such a tool, the data set comprising the characteristics of the tool—the fingerprint—must be compared with the detected signal of the tablet to be verified.

In an advantageous embodiment, the invention relates to a process as described herein, wherein one or more predetermined three-dimensional structures as defined above are located in both punches. Using this process, tablets containing a security feature on both sides are obtained. This ensures a reliable method of verification, as at least one face of the tablet will be in the direction of the optical detection device. This is particular suitable if tablets are verified through a blister package.

Further, the invention relates to a tablet obtained by a process as described herein.

In a fourth aspect, the invention relates to the use of a verification method as described herein for authentication, identification and/or security purposes in connection with tablets.

In a preferred embodiment, the invention relates to the use of optical interferometry microscopy for verification of tablets, in particular for tablets as described in the first aspect of the invention. The described technique has the potential to be implemented in the tablet manufacturing process. The market of pharmaceutical tablet is very huge and there is a need for security solutions in the tablets as this is a demand of the governmental authorities such as the US-FDA.

In a further advantageous embodiment, the verification method as described herein is used for quality control. During production of tablets the above described steps of pressing take place. The thus obtained tablets will be subject to further process steps such as coating and/or packaging in blisters. These process steps may cause damage to the tablet. The verification method as described herein now offers a convenient way of quality control prior to the final packaging as supplied to the customer. Thus, in a further advantageous embodiment, the present invention relates to the use of a verification method as described herein for quality control of tablets.

The following examples are intended to further illustrate the invention without limiting it.

Manufacture of a punch: A topography pattern consisting of mirror-inverted letters "CSEM" was manufactured in a hard chromium-coated steel punch as follows: A thin light-sensitive layer of Microposit S 1800 (Röhm & Haas) was spin-coated on the surface of the punch in a lab with no blue or UV light. The thickness of this layer was approximately 4000 nm. After deposition a soft bake at 100° C. for 15 minutes was carried out. Next the photo resist was exposed by a UV-lamp through a shadow mask with said letters. After the exposure the resist was developed in S303 (Microposit). Immediately after the development step the punch was put in a stop bath with pure water. The temperature of both baths was 30° C., and it is controlled to ±0.2° C. The opened mask was used to transfer the topography structure in the punch surface by a dry-etching step. This etching in the hard punch surface was done by bombardment with Argon ions (Veeco RF 350) with a kinetic energy in the order of 500 eV. At 500 eV the energy is low enough to prevent high penetration of the source ions into the sample but not to the detriment of etching efficiency. After the desired topography structure depth of 4 µm was reached the residual resist was removed leaving the clean punch surface with the topography structure.

Manufacture of tablets: The punch as manufactured above was used in a rotary press to manufacture tablets at a speed of 30000 tablets per hour. The powder mixture used was 73% Lactose Monohydrate, 24% Microcrystalline Cellulose, 1% Aerosil (colloidal silica, anhydrous), 1% Magnesium-stearate and as active agent 1% Na-salicylat. Tablets were pressed with a compacting force of 30 kN. The resulting tablets possess the letters CSEM as a topography pattern. In the pressed tablet core the letters are only very weakly visible. After a colored coating they are no longer visible to the unaided eye. As a comparison, tablets were manufactured using the same starting materials and conditions but a standard punch.

Method of verification: The tablets as manufactured above were measured with the pOCT microscope M1 (Heliotis Inc., Switzerland). The predetermined three-dimensional structures, the topography pattern of the CSEM letter, in the surface of the tablets could be identified. Thus the tablet was verified.

What is claimed is:

1. A verification method for a pharmaceutical tablet, comprising:
    compressing a powder mixture in a die between two punch tools to produce a core of the tablet, the compressing including embossing one or more three-dimensional structures on the surface of the core, and the compressing further including impressing a diffractive microstructure on the surface of the core to define a visible hologram on the tablet in combination with the one or more three-dimensional structures;
    applying a coating over the surface of the core to produce the tablet in finalized form with the one or more three-dimensional structures at an interface between the core and the coating, the coating rendering each of the one or more three-dimensional structures invisible to the unaided eye by appropriate color, thickness, reflection or scattering properties thereof; and
    verifying authenticity of the tablet after production of the tablet by scanning the tablet with an optical interferometry microscope to detect the one or more three-dimensional structures,
    wherein compressing the powder mixture further comprises:
        applying a compression force on the powder mixture with the two punch tools in the range of 5 to 25 kN; and
        completing application of the compression force to finalize production of the core in less than 100 ms, thereby enabling the punch tools to produce up to 30,000 tablets per hour,
    wherein the verification method further comprises selecting materials for inclusion in the powder mixture and the core that provide sufficient properties to enable receipt of the embossed one or more three-dimensional structures and also to enable release from the punch tools at mass production speeds defined by production of up to 30,000 tablets per hour, and wherein selecting materials for inclusion in the powder mixture further comprises including in the core:
        50-80% lactose monohydrate acting as one binding and filling agent;
        10-50% cellulose derivative acting as another binding and filling agent;
        0.1-5% silica acting to improve powder flow during compression;
        0.1-5% of a fatty acid salt acting as a lubricant; and
        0.1-20% of an active ingredient,
    wherein compressing the powder mixture further comprises:
        forming by embossing the one or more three-dimensional structures such that the one or more three-dimensional structures define dimensions in a range of 2 µm to 20 µm in lateral direction and dimensions in a range of 50 µm to 5 µm in vertical direction, the dimensions of the one or more three-dimensional structures rendering these invisible to the unaided eye but visible to the optical interferometry microscope; and
        forming by embossing the one or more three-dimensional structures such that the one or more three-dimensional structures are non-periodic, while the diffractive microstructure defining the visible hologram is periodic in structure.

2. The verification method of claim 1, wherein verifying authenticity of the tablet further comprises:
    recording a data set with the detection device, the data set describing characteristics of the one or more three-dimensional structures; and
    comparing the recorded data set with at least one predefined data set associated with the punch tools.

3. The verification method of claim 2, wherein the die and punch tools include embossing tools used to make the tablet, each of which is associated with one of a plurality of predefined data sets defining characteristics of the corresponding embossing tool, and comparing the recorded data set further comprises:
    confirming whether the recorded data set matches at least one of the plurality of predefined data sets, thereby to confirm that the tablet was manufactured by one of the plurality of embossing tools, which renders the tablet authentic.

4. The verification method of claim 1, further comprising:
    selecting materials for the core and the coating such that an index of refraction of the coating and an index of refraction of the core differ by at least 0.04 real part.

5. The verification method of claim 1, wherein verifying authenticity of the tablet further comprises:
    scanning the tablet with an optical coherence tomograph (OCT) defining the optical interferometry microscope, to thereby detect the one or more three-dimensional structures.

6. The verification method of claim 5, wherein verifying authenticity of the tablet further comprises:
    scanning the tablet with a parallel optical coherence tomograph (pOCT) defining the optical interferometry microscope, to thereby detect the one or more three-dimensional structures.

7. The verification method of claim 1, further comprising: packaging the tablet in a blister pack.

8. The verification method of claim 1, wherein selecting materials for inclusion in the powder mixture further comprises:
   coating particles in the powder mixture with polyvinylpyrrolidone, which improves a compressibility of the particles in the powder mixture during compression.

9. The verification method of claim 1, wherein in the powder mixture, microcrystalline cellulose is used as the cellulose derivative, and magnesium-stearate is used as the fatty acid salt.

* * * * *